United States Patent [19]

Matsumoto et al.

[11] Patent Number: 5,011,922

[45] Date of Patent: * Apr. 30, 1991

[54] PROCESS FOR PURIFYING SUCROSE FATTY ACID ESTERS

[75] Inventors: Shusaku Matsumoto, Kyoto; Yoshio Hatakawa, Higashiosaka; Akihiko Nakajima, Kyoto, all of Japan

[73] Assignee: Dai-Ichi Kogyo Seiyaku Co., Ltd., Kyoto, Japan

[*] Notice: The portion of the term of this patent subsequent to Feb. 26, 2008 has been disclaimed.

[21] Appl. No.: 371,892

[22] Filed: Jun. 23, 1989

[30] Foreign Application Priority Data

Jun. 27, 1988 [JP] Japan .................... 63-158930

[51] Int. Cl.$^5$ .............. C07H 1/00; C07H 13/00; C08B 37/00; C13D 3/00
[52] U.S. Cl. ...................... 536/119; 536/115; 536/120; 536/124; 536/127
[58] Field of Search ............. 536/127, 124, 119, 115, 536/120

[56] References Cited

U.S. PATENT DOCUMENTS 3,792,041  10/1970  Yamagishi et al. ............ 536/119
4,252,834   2/1981  Inamine et al. ............... 426/103

FOREIGN PATENT DOCUMENTS 809815  3/1959  United Kingdom .
958064  5/1964  United Kingdom .

OTHER PUBLICATIONS

Abstract of Japanese Patent Publication No. 8850/67, Derwent Japanese Patents Report, vol. 6, No. 16, 1967, General Organic–p. 4.

Primary Examiner—Ronald W. Griffin
Assistant Examiner—Everett White
Attorney, Agent, or Firm—Armstrong, Nikaido, Marmelstein, Kubovcik & Murray

[57] ABSTRACT

A process for purifying sucrose fatty acid esters included in a reaction mixture formed by a reaction of sucrose and a fatty acid alkyl ester in an organic solvent as reaction medium in the presence of a catalyst, which comprises adjusting the reaction mixture from which a part of the organic solvent as reaction medium may be previously removed and to which water is added to form an aqueous solution, to a neutral pH region, adding a neutral salt and sucrose to the solution to precipitate the sucrose fatty acid ester, filtering off the precipitate, and washing the precipitate with an acidic water. The washed precipitate in the form of slurry is spray-dried to form a dry powder, and the filtrate is contacted with a reverse osmosis membrane to recover sucrose. According to the invention, purified sucrose fatty acid esters can be obtained from the reaction mixture without using an organic solvent as purification solvent, while sucrose can be recovered in high yield.

25 Claims, 1 Drawing Sheet

WATER(%) + TOTAL SALT(%) + TOTAL SUCROSE(%) = 100(%)

FIG. 1

WATER(%) + TOTAL SALT(%) + TOTAL SUCROSE(%) = 100(%)

PROCESS FOR PURIFYING SUCROSE FATTY ACID ESTERS

BACKGROUND OF THE INVENTION

The present invention relates to a treatment of a reaction mixture of sucrose and a fatty acid alkyl ester. More particularly, the present invention relates to an industrially useful process for isolating purified sucrose fatty acid esters from the reaction mixture obtained in the synthesis of sucrose fatty acid esters in an organic solvent medium.

Sucrose fatty acid esters (sugar esters) useful as surface active agents are prepared industrially at present by either a solvent process wherein sucrose is reacted with a methyl ester of a higher fatty acid having 8 to 22 carbon atoms in the presence of a suitable catalyst in an organic solvent such as dimethylformamide or dimethylsulfoxide, as disclosed in Japanese Patent Publication Kokoku No. 35-13102; or an aqueous medium process wherein sucrose is formed into a molten mixture with a fatty acid salt (soap) using water without using an organic solvent, and is then reacted with a higher fatty acid methyl ester in the presence of a catalyst, as disclosed in Japanese Patent Publication Kokoku No. 51-14485.

However, even according to any of these processes, the obtained reaction mixture contains impurities such as the unreacted sucrose, the unreacted fatty acid methyl ester, residual catalyst, soap, free fatty acid, volatile material, etc. in addition to the desired sucrose fatty acid ester. These impurities, at least impurities whose contents exceed the specified amounts must be removed prior to the sucrose fatty acid ester being put on the market. Particularly, in case of sucrose fatty acid esters used as a food additive which requires a high purity, removal of the solvent (volatile material) remaining in the product is very important in view of strict regulation, e.g. provision by FDA, U.S.A. according to which allowable content of remaining dimethylsulfoxide in sucrose fatty acid esters is at most 2 p.p.m. [Fed. Regist., 51(214), 40160-1].

In general, the conversion of sucrose is low. For example, in case of the process using dimethylformamide as the reaction medium, the conversion is at most 50%. Accordingly, recovery of the unreacted sucrose is also important.

In order to remove the remaining organic solvents and to recover the unreacted sucrose from the reaction mixture (namely crude sucrose fatty acid esters), various processes for the purification of crude product have hitherto been proposed. These purification processes usually require a large amount of organic solvents. However, in the production of sucrose fatty acid esters on an industrial scale, the use of a large amount of organic solvents has the following disadvantages: (1) risk of explosion and fire, (2) provision of explosion and fire prevention means to electric devices, (3) application of closed system to production equipment for explosion and fire prevention, (4) requirement of fireproof construction for entire building by way of precaution against explosion and fire, (5) rise in fixed cost due to the items (2), (3) and (4), (6) rise in materials cost due to loss of solvent, (7) contamination of the product with remaining solvent, and (8) adverse influence on health of workers, and increase of cost resulting from increase in labor required for the prevention therefor.

In view of these circumstances, it has been desired to develop a purification technique capable of removing the unreacted sucrose and other impurities from the crude reaction mixture without using organic solvents.

Thus, purification processes using no organic solvent have been proposed. For example, as representative methods, there have been known (1) a method wherein a sucrose fatty acid ester is precipitated by addition of an acidic aqueous solution to the reaction mixture, as disclosed in British Patent No. 809,815 and (2) a method wherein a sucrose fatty acid ester is precipitated by addition of an aqueous solution of a common neutral salt to the reaction mixture, as disclosed in Japanese Patent Publication Tokkyo Kokoku No. 42-8850.

However, these methods have disadvantages. When an acidic aqueous solution, for example, hydrochloric acid, is added to the reaction mixture as in the method (1), the sucrose fatty acid ester immediately deposits, but the unreacted sucrose is easily decomposed and converted into glucose and fruit sugar. This cannot be avoided even if the addition is conducted at a low temperature (e.g. 0° to 5° C.). Accordingly, the recovery and reuse of the unreacted sucrose becomes difficult.

The addition of an aqueous solution of a neutral salt such as sodium chloride or Glauber's salt, as in the method (2), causes sucrose fatty acid esters to deposit rapidly. In this case, decomposition of unreacted sucrose does not occur, but the monoester which is an effective component in the product is dissolved in the aqueous phase. Consequently, not only does the dissolution results in a large loss of the product, but also it is a hindrance particularly to production of sucrose fatty acid esters having a high HLB which are recently in great demand.

Also, in Japanese Patent Publication Tokkyo Kokai No. 51-29417, it is proposed to utilize the finding a mixture of water and a solvent used for purification (hereinafter referred to as "purification solvent") separates into an upper light layer and a lower heavy layer. Generally, the lower layer contains a large amount of water and, therefore, the unreacted sucrose, which is hydrophilic, and the salt derived from a catalyst used in the synthesis of sucrose fatty acid esters are dissolved in the lower layer. Since the upper layer contains the purification solvent in a large quantity, compounds having a small polarity such as sucrose fatty acid esters, fatty acids and unreacted fatty acid methyl esters are dissolved in the upper layer. On the other hand, the solvent used for the reaction such as dimethylsulfoxide is dissolved not only in the lower layer, but also inconveniently dissolved in the upper layer. Consequently, it is impossible to completely separate the reaction solvent only by this method. The product is contaminated with a trace amount of the reaction solvent, and the removal of such a trace amount of the solvent further requires a large amount of purification solvent.

In order to industrially realize the purification of crude sucrose fatty acid esters using water, it is very important that the reaction solvent and the purification solvent are completely removed and moreover sucrose and the product are not lost.

Other important problems which must also be taken into consideration are recovery of the unreacted sucrose and drying of wet product, incident to the use of water as a purification solvent.

Since the purification of the reaction mixture with the use of water is based on the difference in water solubility between a sucrose fatty acid ester and unreacted sucrose, migration of a large amount of unreacted sucrose into an aqueous phase cannot be avoided. The manufacture of sucrose fatty acid esters cannot be industrially accepted unless the dissolved sucrose is recovered. Accordingly, it is also very important to efficiently recover the sucrose which has migrated into an aqueous phase upon purification.

The water-containing sucrose fatty acid ester which has been separated from the reaction mixture to be dried, is usually in the form of an aqueous solution when the water content is over 80% by weight, and in the form of a slurry when the water content is less than 80% by weight. In general, an aqueous solution of a sucrose fatty acid ester shows peculiar viscosity behavior such that the viscosity rapidly increases from about 40° C., reaches maximum at about 50° C. and rapidly drops over 50° C. Some problems are encountered in removing the water from the sucrose fatty acid ester in the form of an aqueous solution or slurry. The evaporation of water by heating under a vacuum, for example, using a usual agitated vacuum dryer, is practically difficult because of marked foaming. Moreover, when the evaporation is conducted at a high temperature and the contacting time with the heating source is long, not only is the sucrose fatty acid ester decomposed, resulting in marked coloration or caramel formation, but also the acid value is raised by free fatty acid formed by decomposition, as disclosed in Japanese Patent Publication Tokkyo Kokoku No. 37-9966. In particular, due to the property of sucrose fatty acid esters that the softing point or melting point is low (for example, sucrose monostearate having a melting point of about 52° C., and sucrose distearate having a melting point of about 110° C.), the sucrose fatty acid ester itself tends to be hydrated at the final stage of evaporation of the water. This makes the dehydration more difficult. In addition, dehydration is difficult because the latent heat of evaporation of water is very high (more than 500 kcal/kg $H_2O$) and the evaporation temperature is high.

Other usual drying methods are also not suitable for preparing dry sucrose fatty acid esters. For example, in the case of using a flash dryer wherein a slurry is continuously heated, fed to a vacuum chamber and released thereto, various difficulties are encountered when a sufficient drying is desired because of the large latent heat of water. Even if these difficulties are overcome, the sucrose ester dehydrated and dried under a vacuum is in the molten state and, therefore, it requires a pulverization step after taking it out of the drier and cooling to less than the melting point to solidify, for instance, by blowing cold air. In addition to the requirement of many steps, there is a risk of dust explosion in the final pulverization step.

Accordingly, it is also important to solve the problems encounted by drying in the purification of sucrose fatty acid esters when using water as the purification solvent.

It is a primary object of the present invention to provide a process for obtaining a purified sucrose fatty acid ester from the reaction mixture without using organic solvents as the purification solvent.

A further object of the invention is to provide a process for removing a remaining organic solvent used as a reaction medium in the synthesis of sucrose fatty acid esters from the crude product.

A still further object of the invention is to provide a process for purifying the crude product of sucrose fatty acid esters without using an organic solvent as the purification solvent and without substantial loss of the sucrose fatty acid esters.

Another object of the invention is to provide a process for easily preparing a dry powder of a sucrose fatty acid ester having an improved purity and without deteriorating the quality in the drying step, while recovering the unreacted sucrose.

These and other objects of the present invention will become apparent from the description hereinafter.

SUMMARY OF THE INVENTION

The present inventors have made experiments about salting out in the purification of crude product using water as the purification medium in order to achieve the following purposes: namely (1) minimizing the amount of sucrose fatty acid esters dissolved in an aqueous phase, and if possible, decreasing it up to zero so as to precipitate the whole of sucrose fatty acid esters, (2) preventing decomposition of unreacted sucrose, (3) separating the reaction solvent from the sucrose fatty acid esters by dissolving the remaining reaction solvent in the aqueous phase, (4) purifying the precipitated sucrose fatty acid esters and forming a dry powder thereof, and (5) efficiently recovering the unreacted sucrose from the filtrate (or supernatant) obtained by removing the above-mentioned precipitate.

It has now been found that when sucrose and a neutral salt are dissolved in an aqueous solution of the reaction mixture, the whole of the sucrose fatty acid esters are precipitated under a combination of proper pH, temperature, concentrations of neutral salt and sucrose, and amount of water, and moreover, surprisingly, the reaction solvent is dissolved in the aqueous phase with the unreacted sucrose. Thus, it has been found that the remaining volatile material (remaining reaction solvent) can be transferred completely into the aqueous phase, substantially preventing the loss of sucrose fatty acid esters, by utilizing the above phenomenon, namely by dissolving the precipitated sucrose fatty acid esters again in water and repeating the precipitation procedure by the addition of an aqueous solution of the neutral salt and sucrose, and that the unreacted sucrose can be efficiently recovered from the reaction mixture by contacting the residual liquid after removal of the above precipitate with an adequate reverse osmosis membrane.

Accordingly, in one of the aspects of the present invention, there is provided a process for removing a volatile material from a reaction mixture in synthesis of a sucrose fatty acid ester by a reaction of sucrose and a fatty acid alkyl ester in an organic solvent, said reaction mixture containing the unreacted sucrose, the unreacted fatty acid alkyl ester, a catalyst, a soap, a fatty acid and the organic solvent as a volatile material, which comprises adjusting the reaction mixture to a neutral pH region, adding water, a neutral salt and sucrose to the reaction mixture to transfer the volatile material into the aqueous phase with precipitation of the sucrose fatty acid ester, unreacted fatty acid alkyl ester, soap and fatty acid, and separating the resulting precipitate.

It has also been found that the neutral salt and sucrose accompanied with the precipitated sucrose fatty acid ester can be substantially removed by washing the precipitate with an acidic water having an appropriate pH, whereby the purified sucrose fatty acid ester is obtained.

Thus, in another aspect, the present invention provides a process for purifying a sucrose fatty acid ester included in a reaction mixture formed by a reaction of sucrose and a fatty acid alkyl ester in an organic solvent, which comprises adjusting the reaction mixture to a neutral pH region, adding water, a neutral salt and sucrose to the reaction mixture to precipitate the sucrose fatty acid ester, filtering off the resulting precipitate, and washing the precipitate with an acidic water.

Further, it has been found that a dry powder of the sucrose fatty acid ester can be obtained without deteriorating the quality by spray-drying an aqueous solution or slurry of the precipitated sucrose fatty acid ester.

Accordingly, in still another aspect of the present invention, there is provided a process for preparing a powder of sucrose fatty acid ester from a reaction mixture formed by a reaction of sucrose and a fatty acid alkyl ester in an organic solvent, said reaction mixture containing the sucrose fatty acid ester, unreacted reactants and impurities, which comprises adjusting the reaction mixture to a neutral pH region, adding water, a neutral salt and sucrose to the reaction mixture to precipitate the sucrose fatty acid ester, separating the resulting precipitate from the aqueous phase, washing the precipitate with an acidic water followed by neutralization, spray-drying the precipitate in the form of an aqueous solution or slurry to form a dry powder, and bringing the aqueous phase into contact with a reverse osmosis membrane to recover sucrose.

DETAILED DESCRIPTION

The process of the present invention is suitable for purification of the reaction mixture obtained in the synthesis of sucrose fatty acid esters (hereinafter referred to as "SE") by a known reaction using an organic solvent as reaction solvent.

In the synthesis of SE using an organic solvent as reaction medium, generally the solvent, for example, dimethylsulfoxide is added to dissolve a mixture of sucrose and a fatty acid methyl ester in an amount of several times the total amount of sucrose and the fatty acid methyl ester. They are reacted in the presence of an alkaline catalyst such as potassium carbonate ($K_2CO_3$) under reduced pressure of 20 to 30 Torrs at a temperature of 80° to 90° C. for several hours, whereby the SE is easily produced in a conversion of at least 90% (based on the fatty acid methyl ester).

In order to deactivate the alkaline catalyst, e.g. $K_2CO_3$, included in the resulting reaction mixture, an equivalent amount of an organic acid such as lactic acid or acetic acid, or a mineral acid such as hydrochloric acid or sulfuric acid is added to the reaction mixture. By this neutralization, the catalyst changes to a corresponding salt, e.g. a potassium salt such as potassium lactate, according to the kind of the acid used in the neutralization.

The reaction solvent (e.g. dimethylsulfoxide) is then distilled away under a vacuum. The thus obtained residue (reaction mixture after subjected to the neutralization and vaporization of solvent) has approximately the following composition.

| Ingredients | % by weight |
| --- | --- |
| SE | 15.0 to 74 |
| Unreacted sucrose | 1.0 to 80 |
| Unreacted fatty acid methyl ester | 0.5 to 10 |
| Salt derived from $K_2CO_3$ | 0.05 to 7 |
| Soap | 1.0 to 10 |
| Fatty acid | 0.5 to 10 |
| Volatile material (remaining reaction solvent) | 5.0 to 30 |

In that case, the proportion of the monoester in the SE is from 10 to 75% by weight and the proportion of di- and higher esters is from 90 to 25% by weight.

Also, the acid radical mainly included in each of the fatty acid methyl ester, soap and fatty acid is usually a saturated acid radical having 16 to 22 carbon atoms common to them.

To the reaction mixture from which the solvent is partly distilled away and which has the above-mentioned composition, water is added in a water/reaction mixture ratio of 5:1 to 40:1 by weight, preferably 20:1 by weight, while the pH is adjusted to 6.2 to 8.2, preferably 7.5.

When the ratio of water to the reaction mixture is less than 5, the viscosity of the obtained aqueous solution is high and the following procedures become difficult. Also, when excess water is added to the reaction mixture such that the weight ratio of water to the reaction mixture exceeds 40, the viscosity of the obtained aqueous solution is low and accordingly the following procedures become easy and also the desired removal of reaction solvent can be accomplished, but a large energy cost is required in removing water upon recovery of unreacted sucrose, etc., thus the economy is impaired.

In order to prevent decomposition of the desired SE, it is preferable to adjust the aqueous solution of the reaction mixture to a pH of 6.2 to 8.2. When the pH is more than 8.2, there is a possibility that SE is quantitatively hyrdolyzed by an alkali. On the other hand, even in a weak acidic region of less than pH 6.2, there is a fear of acid hydrolysis of SE, for example, when it is exposed to a high temperature over 90° C.

To the thus pH-adjusted aqueous solution of the reaction mixture are added a neutral salt and sucrose, preferably by keeping at a temperature of 50° to 80° C. in order to salt out SE rapidly. In that case, it is preferable that the neutral salt to be added satisfies the following equation (1):

$$\frac{\text{Amount of neutral salt to be added} + \text{Amount of salt formed from catalyst}}{\text{Amount of water} + \text{Total amount of salts} + \text{Total amount of sucrose}} = \quad (1)$$

0.015 to 0.12 by weight wherein the total amount of salts means the sum of the neutral salt to be added and the salt formed by neutralization of the catalyst used in the production of SE, and the total amount of sucrose means the sum of the sucrose to be added and the unreacted sucrose included originally.

Also, it is preferable to add sucrose in an amount satisfying the following equation (2):

$$\frac{\text{Amount of sucrose to be added} + \text{Amount of unreacted sucrose}}{\text{Amount of water} + \text{Total amount of salts} + \text{Total amount of sucrose}} = \quad (2)$$

0.025 to 0.20 by weight

In addition to the above equations (1) and (2), it is also preferable that the total amount of salts and the total amount of sucrose satisfy the following equation (3):

$$\frac{\text{Total amount of salts}}{\text{Total amount of sucrose}} = \frac{0.4 \text{ to } 0.6}{\text{(preferably 0.5) by weight}} \quad (3)$$

Any of the neutral salts can be used so long as they are soluble in water and nontoxic. Representative examples of the neutral salt are, for instance, sodium chloride, Glauber's salt ($Na_2SO_4 \cdot 10H_2O$), potassium lactate and potassium acetate.

It has been found that when the aqueous solution containing SE precipitate obtained by adding neutral salt and sucrose so as to satisfy the equations (1), (2) and (3) is heated to a temperature of 50° to 80° C., approximately the whole amount of SE is precipitated even if the content of the volatile material (remaining reaction solvent) in the reaction mixture widely ranges from 5.0 to 30.0% by weight. This is a peculiar phenomenon and is of important value in connection with the objects of the present invention. By utilizing this phenomenon, SE can be separated in the form of a slurry or cake from the whole sucrose (unreacted sucrose and the sucrose added for the precipitation), the volatile material, the salt derived from the catalyst and the neutral salt all of which have transferred to the aqueous phase.

Figure 1:
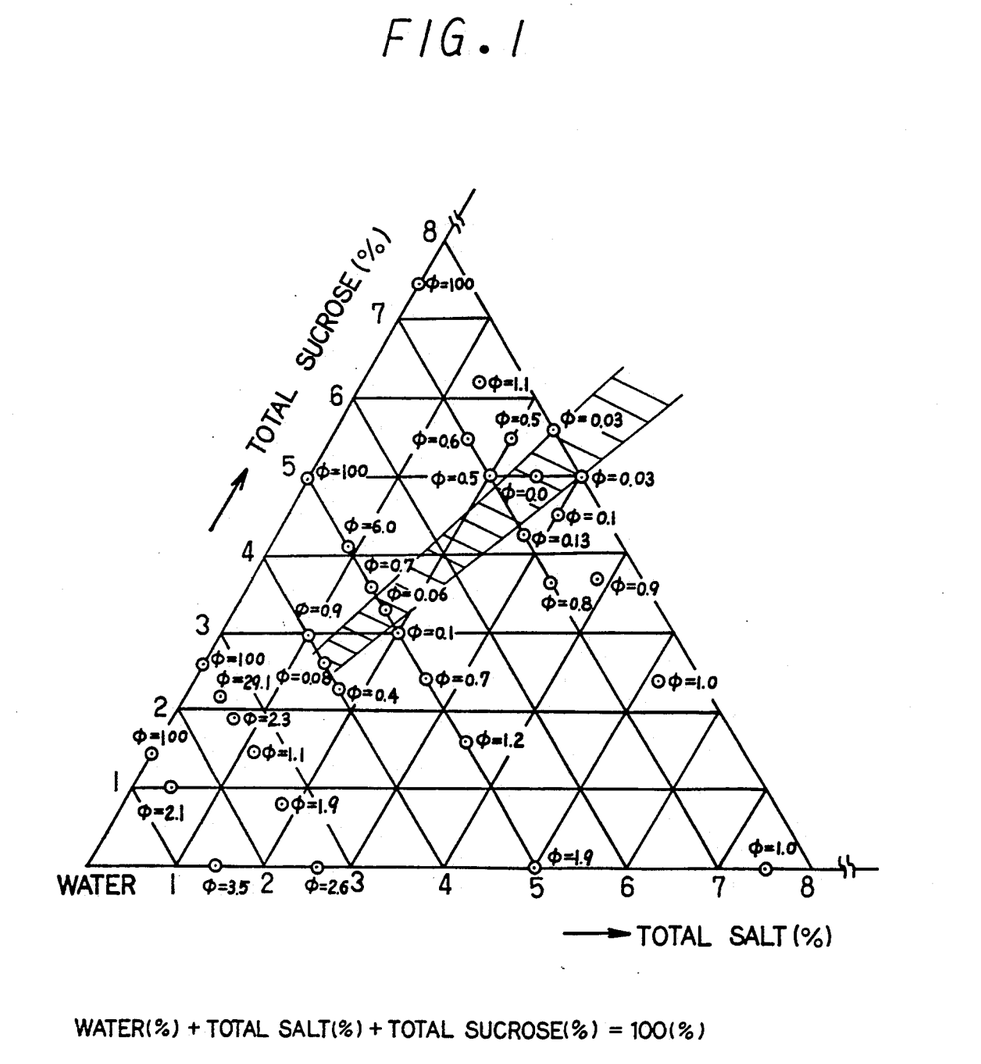
FIG. 1 is a triangular graph showing the relationship between the amount of each of water, total sucrose and total salt, and the amount of sucrose fatty acid ester dissolved in aqueous phase.

FIG. 1 is a triangular graph showing the above-mentioned phenomenon in more detail. When Y (g) is the weight of SE dissolved in an aqueous phase and X (g) is the weight of SE precipitated, the weight percentage ($\phi$ %) of SE dissolved in the aqueous phase based on the total SE (X+Y) is shown by the following equation:

$$\phi = \frac{Y}{X + Y} \times 100 \text{ (\% by weight)}$$

The change in the value $\phi$ under the following conditions is shown in the accompanying drawing.

| Conditions | |
|---|---|
| Temperature = 80° C. | |
| pH = 7.5 | |
| Water/reaction mixture = 7.4/1 by weight | |
| Fatty acid radical: stearic acid | |
| Composition of reaction mixture (% by weight) | |
| SE | 29% |
| Unreacted sucrose | 35% |
| Unreacted fatty acid methyl ester | 2% |
| Salt derived from catalyst | 1% |
| Soap | 3% |
| Fatty acid | 1% |
| Volatile material (remaining reaction solvent) | 29% |
| Composition of SE (% by weight) | |
| Monoester | 73% |
| Di- and higher esters | 27% |

In the drawing, the total salt and the total sucrose are as defined above, and the sum of water, total salt and total sucrose is 100% by weight.

The shaded part in FIG. 1 shows the region simultaneously satisfying the equations (1), (2) and (3) which has been discovered by the present inventors.

By adding the determined amounts of sucrose and neutral salt to be dissolved in the aqueous solution of the reaction mixture so as to fall within the shaded region, the volatile material (remaining reaction solvent), salt derived from catalyst, neutral salt added and the whole sucrose are dissolved in the aqueous phase with precipitation of approximately the whole amount of SE, whereby they can be completely separated from the precipitated SE.

The precipitated SE can be recovered by a usual method, for example, by filtration.

It is also important to selectively separate and recover only sucrose from the thus treated aqueous solution from which the precipitated SE has been removed, and thus which contains sucrose separated with water, the salt derived from catalyst ($K_2CO_3$), the neutral salt added for salting out and the volatile material. The present inventors have found that utilization of a reverse osmosis membrane is particularly effective for this purpose. After separating the precipitated SE in a usual manner, for example, by filtration, the filtrate is subjected to reverse osmosis.

It is expected that if a fractionation molecular weight ranging from 130 to 200 is selected as that of the reverse osmosis membrane, the unreacted sucrose (molecular weight: 342) and the SE (molecular weight: more than 600) which has incidentally leaked into the filtrate in the prior steps such as the salting out step, would be filtered off without any problem by the reverse osmosis treatment. On the other hand, substances having a molecular weight less than the fractionation molecular weight of 130 to 200, namely the salt derived from catalyst such as potassium lactate (molecular weight: 128), the neutral salt added, and the volatile component such as dimethylsulfoxide (molecular weight: 78) would pass through fine pores of the reverse osmosis membrane without any problem.

As a result of conducting a large number of experiments on the basis of the above presumption, it has been found that when an aqueous solution containing sucrose, the salt derived from catalyst, the neutral salt added in the salting out step and the volatile material, and sometimes further a slight or trace amount of SE, is brought into contact with a reverse osmosis membrane having a fractionation molecular weight of about 150 to about 200 at a temperature of 40° to 60° C. under a pressure, the salt derived from catalyst, the neutral salt and the volatile material easily pass with water through fine pores of the membrane. By this reverse osmosis procedure, low molecular weight substances such as the salts, volatile material and water are separated from the impure aqueous sucrose solution (which may contain a slight amount of SE) to thereby form the concentrated aqueous solution of crude sucrose. An aqueous sucrose solution having a higher purity can be obtained by dissolving the concentrate in fresh water again and subjecting the solution to the reverse osmosis treatment in the same manner, and if necessary, further repeating these procedures.

The temperature of the aqueous solution to be fed to the reverse osmosis is important for obtaining a good result. If the temperature is lower than 40° C., the treating ability is remarkably lowered. Accordingly, it is desirable to select a temperature over 40° C. from a practical point of view. On the other hand, it is advisable to conduct the treatment at a temperature below 60° C., since there is a possibility that the heat resistance of the reverse osmosis is changed at a temperature over 60° C. The pH of the aqueous solution to be treated is also important, and the pH ranging from 6.2 to 8.2 is preferred because a fear of influence on the quality of sucrose is minimized.

Recently, various reverse osmosis membranes have been put on the market from various companies. Among them, for instance, reverse osmosis membranes of a polyamide or a polyether have excellent properties such as durability, heat resistance, acid resistance and alkali resistance, fungus resistance and pressure resistance. Such membranes are commercially available, for example, under a trade mark "SU-200" from Toray Engineering Kabushiki Kaisha, which has a fractionation molecular weight of about 200 and is suitable to attain the objects of the invention.

In the case of using the reverse osmosis membrane with the fractionation molecular weight of about 200, the treatment of the aqueous solution can be achieved with an industrially acceptable capacity by adjusting the upper limit of the concentration of the solute in the aqueous solution to be supplied to the membrane to about 20% by weight, preferably about 15% by weight.

When the solute concentration is more than 20% by weight, it is difficult to pass water, the salt derived from the catalyst and the volatile material through fine pores of the membrane, and accordingly the pressure to be applied as the actuation force for reverse osmosis must be increased, thus resulting in increase of the area of the reverse osmosis membrane. This is also very uneconomical because of the necessity of great electric power. On the other hand, when the aqueous solution contains the solute in a concentration of not more than about 8–15% by weight, it is sufficiently possible to industrially isolate sucrose.

For example, when passing an aqueous solution having the composition shown in Table 1 through the reverse osmosis membrane "SU-200" with an effective area of 8 m² per unit at 50° C. and pH 7.5 and under a pressure applied as the actuation force for reverse osmosis of 56.0 kg/cm²G, the sucrose isolation velocity of 7.3 kg/hour is achieved. Other reverse osmosis membranes similar to "SU-200", commercially available from companies other than Toray Engineering Kabushiki Kaisha, also give similar results. In all cases, sucrose dissolved in the aqueous solution can be recovered in a good yield together with SE.

TABLE 1

| Components | Weight (kg) |
| --- | --- |
| Sucrose fatty acid ester (stearate) | 0.4 |
| Sucrose | 39.0 |
| Potassium lactate | 9.0 |
| Volatile material (reaction solvent) | 5.0 |
| Soap and fatty acid | 0.1 |
| Subtotal | 53.5 |
| Water | 481.0 |
| Total | 534.5 |

Like this, by repeating the reverse osmosis membrane treatment, the salt derived from the catalyst, the added neutral salt and the volatile material are sufficiently removed from the aqueous solution. The thus obtained aqueous solution containing sucrose can keep a sucrose concentration of about 15 to 20% by weight. It is economically disadvantageous as well as technical difficulty to obtain the aqueous solution of sucrose with a concentration of more than 20% by weight using the reverse osmosis means. Accordingly, when it is desired to obtain the aqueous solution of sucrose having a sucrose concentration of more than 20% by weight, the solution is concentrated by using a usual concentration apparatus such as a multiple effect evaporator to the desirable concentration such as not less than 50% by weight. Thus recovered sucrose can be reused in the preparation of SE as a raw material or used for other purposes.

The SE precipitated and separated in the salting out step is in the form of a slurry. It still contains a slight amount of impurities such as the volatile material, salts and sucrose. These impurities can be easily removed by treating the slurry with an acidic water.

An aqueous slurry or cake of crude SE obtained in the salting out step is washed with an aqueous solution of an acid having a pH of 3.0 to 5.5. The acid is not particularly limited. Preferable examples of the acid are, for instance, a mineral acid such as hydrochloric acid or sulfuric acid, and an organic acid such as acetic acid or lactic acid. Preferably, the acid solution is kept at a temperature of 10° to 40° C. By this treatment, the impurities such as volatile material, sucrose, neutral salt and catalyst-derived salt can be transferred into the acidic water with minimized transfer of SE into water. When the temperature of the acidic water is higher than 40° C., the viscosity rises to hinder the operation in addition to a fear of acid decomposition of SE if the operation is required for a long period of time, for example, over several months. On the other hand, it is uneconomical to keep the acidic water at a low temperature lower than 10° C., because a cooling device is required therefor. Accordingly, the acid solution treatment is effected usually at a temperature of 10° to 40° C., preferably at ordinary temperature.

Only the above-mentioned four components included in the cake or slurry, namely volatile material (reaction solvent), sucrose, neutral salt and salt formed by neutralization of the catalyst, should be removed from the cake or slurry by the acid treatment. Accordingly, it is desirable that the SE cake or slurry is in the form of particles as small as possible so that the impurities are easily released or eluted into the water upon washing with acidic water. This can be efficiently attained by conducting the washing in a device having an ability to break into small particles, for example, a mixer (such as "homomixer" made by Tokushu Kiki Kogyo Kabushiki Kisha), a homogenizer, or a colloid mill.

Although substantially the whole amounts of the above-mentioned impurities included in the SE cake or slurry can be transferred into the acidic water, it is unavoidable that a slight amount of SE is eluted into the acidic water. This tendency of elution increases with increasing the monoester content in SE. Accordingly, the elution can be decreased by increasing the content of diesters, triesters or the like in the SE cake or slurry.

The removal of impurities by washing of the SE cake with acidic water can be made more complete by repeating the washing procedure or increasing the amount of acidic water, thus it is possible to obtain a substantially pure SE.

The thus purified SE containing water is in the form of a slurry, and its pH is on the acid side. Preferably, the slurry is adjusted to a neutral pH region. Usually, the slurry is neutralized with a base compound such as sodium hydroxide.

The neutralized slurry is free from unreacted sucrose, sucrose added for salting out, a salt derived from the reaction catalyst, the volatile material and the neutral salt added for salting out. It contains SE, unreacted fatty acid alkyl ester such as methyl ester, a soap and a fatty acid and in many cases, it is composed of 1 to 50% by weight of the solid matter and 99 to 50% by weight of water.

In view of the drying in the next step, it is preferable that the solid content of the slurry is at most about 40% by weight. However, an excessively low solid content is undesirable from the viewpoint of energy cost for drying. Usually, a solid content of not less than 4% by weight is economical.

In the present invention, spray drying is utilized in drying the SE slurry. This drying means is the optimum for drying the SE slurry having a solid content of 4 to 40% by weight, and has many advantages as compared with other drying methods. As mentioned before, in case of using a usual vacuum dryer as represented by a so-called agitated vacuum dryer, or a flash dryer, deterioration of the quality such as a rise in acid value of SE product, coloration or caramel formation is unavoidable due to peculiar viscosity characteristics and low softening or melting point of SE, and in the latter case, a risk of dust explosion cannot be disregarded. The spray drying according to the present invention can solve these problems.

In the present invention, the wet SE in the form of a slurry is continuously fed to a spray drying tower by a pump, dispersed in the form of mist through a nozzle or by a centrifugal force of a rotary disk, and brought into contact with a dry air stream. Since the surface area of water evaporation is made extremely large by spray drying, dehydration and drying can be completed in a very short time, e.g. in several seconds after spraying. The rotary disc type dryer is preferred from the viewpoint of the high viscosity of the slurry.

The slurry fed to the spray drying tower is kept at a temperature of 40° to 80° C., preferably 40° to 60° C. in consideration of quality. In case of spraying the slurry by means of a rotary disk, the number of rotations thereof is from 15,000 to 24,000 r.p.m. when the diameter of the disk is from 5 to 10 cm.

The air passed through the tower should have a heat energy sufficient to evaporate water included in the slurry, and accordingly when the temperature of the air is low, a large quantity of air is required as a matter of course. The temperature of the air can be selected from a range of 10° to 100° C., but in consideration of drying efficiency and prevention of thermal decomposition of the sucrose ester product, the temperature of the air is preferably selected from a range of 60° to 80° C.

The humidity of the air passed is also important as well as the temperature, and it is economical that the absolute humidity of the air is from 0.008 to 0.05 kg water/kg dry air, especially from 0.01 to 0.04 kg water/kg dry air.

The solid concentration of the slurry to be fed to the spray drying tower is preferably from 4 to 40% by weight. When the solid concentration is more than 40% by weight, the viscosity is remarkably increased. As a result, the size of the mist becomes relatively large, and as much, the drying is delayed and the particles are easily stuck to the wall of the dryer. When the solid concentration is less than 4% by weight, mist of fine particles is easy to be formed and the drying becomes easy, but a larger energy is required for drying.

The parameters such as volume, diameter and height of the spray drying tower is determined on the basis of the above-mentioned spraying conditions. Under appropriate conditions, powder of the sucrose fatty acid ester having a water content of not more than 5% by weight can be continuously taken out from the lower part of the tower. The obtained dry product is very excellent in quality because of short heat time, and also this drying work does not require many hands.

Like this, according to the purification technique using water of the present invention, the volatile material (reaction solvent) remaining in the reaction mixture containing SE produced by a reaction of sucrose and a fatty acid alkyl ester can be easily removed without using an organic solvent as a purification solvent, while sucrose can be easily recovered in a high purity. Further, impurities included in the crude SE from which the volatile material and sucrose have been removed, can be easily removed by washing the crude SE with an acidic water. From the thus purified SE, a dry powder of SE having a high purity can be easily obtained by spray drying without imparing the quality.

The present invention is more specifically described and explained by means of the following Examples in which all % are by weight unless otherwise noted. It is to be understood that the present invention is not limited to these Examples.

EXAMPLE 1

A reaction solvent was distilled away in a usual manner from a reaction mixture formed by a reaction of sucrose and methyl setearate according to the solvent method, and it was neutralized with lactic acid to give a residue having the composition shown in Table 2.

TABLE 2

| Ingredients | Amount (%) | Amount (g) |
|---|---|---|
| SE stearate* | 35.2 | 35.2 |
| Unreacted sucrose | 37.5 | 37.5 |
| Unreacted fatty acid methyl ester (methyl stearate) | 1.5 | 1.5 |
| Potassium lactate | 1.2 | 1.2 |
| Soap | 2.1 | 2.1 |
| Stearic acid | 1.3 | 1.3 |
| Dimethylsulfoxide (reaction solvent) | 21.2 | 21.2 |
| Total | 100 | 100 |

(Note): *The stearate had a monoester content of 70% and a di- or higher-ester content of 30%.

After it was dried, to 100 g of the dried matter was added 2,000 g of water to dissolve it.

To the obtained aqueous solution were added 62.5 g of sucrose and 97.6 g of a 50% aqueous solution of potassium lactate and the temperature was elevated to 75° C. The resulting precipitate was filtered off to give a cake (solid matter: 55%), and it was dried at 80° C. in a vacuum. The composition of the dried cake is shown in Table 3.

TABLE 3

| Ingredients | Amount % | Amount g |
|---|---|---|
| SE | 79.5 | 35.0 |
| Unreacted fatty acid methyl ester | 3.4 | 1.5 |
| Soap | 4.8 | 2.1 |
| Fatty acid | 3.0 | 1.3 |
| Dimethylsulfoxide | 2.5 | 1.1 |
| Sucrose | 5.8 | 2.5 |
| Others | 1.0 | 0.5 |

TABLE 3-continued

| Ingredients | Amount % | g |
|---|---|---|
| Total | 100 | 44.0 |

Measurement of the filtrate according to gel permeation chromatography (GPC) indicated that there was no SE in the filtrate and that 95% of dimethylsulfoxide accompanied as the reaction solvent was removed.

EXAMPLE 2

The procedure of Example 1 was repeated except that 28.5 g of sucrose and 65.6 g of a 50% aqueous solution of potassium lactate were added to the aqueous solution of the reaction mixture. The composition of the dried precipitate is shown in Table 4.

TABLE 4

| Ingredients | Amount % | g |
|---|---|---|
| SE | 79.3 | 34.9 |
| Unreacted fatty acid methyl ester | 3.4 | 1.5 |
| Soap | 4.8 | 2.1 |
| Fatty acid | 3.0 | 1.3 |
| Dimethylsulfoxide | 2.5 | 1.1 |
| Sucrose | 5.5 | 2.4 |
| Others | 1.5 | 0.7 |
| Total | 100.0 | 44.0 |

The amount of SE included in the filtrate was measured according to GPC to determine the loss of SE. The result of GPC indicated that the SE loss was only 0.02 g (0.06% of that included in the original reaction mixture) and that 95% of dimethylsulfoxide used as the reaction solvent was transferred into the filtrate.

EXAMPLE 3

The procedure of Example 1 was repeated to give a dried cake having the composition shown in Table 3.

To 44 g of the dried cake was added 56 g of water to give a slurry, and 2,000 g of an aqueous solution of hydrochloric acid (pH 3.5) of room temperature was added to the slurry, whereby a milky precipitate of SE was rapidly formed.

The obtained acidic aqueous solution of pH 3.5 containing the precipitate was stirred in a homomixer (made by Tokushu Kiki Kogyo Kabushiki Kaisha) to uniformly break the precipitate into small particles. The precipitate was filtered off, adjusted to pH 7.3, and dried at 80° C. in a vacuum. The composition of the obtained solid matter is shown in Table 5.

TABLE 5

| Ingredients | Amount % | g |
|---|---|---|
| SE | 86.7 | 32.0 |
| Unreacted fatty acid methyl ester | 4.1 | 1.5 |
| Soap | 5.3 | 2.0 |
| Fatty acid | 3.3 | 1.2 |
| Dimethylsulfoxide (reaction solvent) | 0.2 | 0.07 |
| Sucrose | 0.3 | 0.10 |
| Potassium salt | 0.1 | 0.05 |
| Total | 100.0 | 36.92 |

EXAMPLE 4

The procedure of Example 2 was repeated to give a dried cake having the composition shown in Table 4.

To 44 g of the dried cake was added 56 g of water to give a slurry, and 3,000 g of an aqueous solution of acetic acid (pH 4) having room temperature was added to the slurry to form quickly a milky precipitate of SE.

The acetic acid solution of pH 4 containing the precipitate was placed in a homomixer to break the precipitate to small particles, and was centrifuged. The obtained slurry of the precipitate was adjusted to pH 7.3 and dried at 80° C. under vacuum to give a solid matter having the composition shown in Table 6.

TABLE 6

| Ingredients | Amount % | g |
|---|---|---|
| SE | 85.53 | 30.2 |
| Unreacted fatty acid methyl ester | 4.2 | 1.5 |
| Soap | 5.9 | 2.1 |
| Fatty acid | 4.0 | 1.4 |
| Dimethylsulfoxide (reaction solvent) | 0.11 | 0.04 |
| Sucrose | 0.20 | 0.07 |
| Potassium salt | 0.06 | 0.02 |
| Total | 100.00 | 35.33 |

EXAMPLE 5

A reaction solvent was distilled away from the reaction mixture in the same manner as in Example 1 to give the residue having the composition shown in Table 2.

Then, the residue was dried, and 100 g of the dried matter was dissolved in 2000 g of water, salted-out, filtered and dried in the same manner as in Example 1 to give the cake having the composition shown in Table 3.

To 44 g of the cake described in Table 3 was added 2,000 g of an aqueous solution of hydrochloric acid (pH 3.5) having room temperature, resulting in quick formation of a white precipitate of SE.

After the acidic aqueous solution of pH 3.5 containing the precipitate was thoroughly stirred in a homomixer, the precipitate was filtered off. The washing procedure wherein to the aqueous solution of hydrochloric acid was added to the precipitate, stirred and filtered, was further repeated twice. The thus obtained slurry of the precipitate was adjusted to pH 7.5 with sodium hydroxide. The obtained slurry had a weight of 150.8 g and a solid content of 25%. The composition of the dried precipitate is shown in Table 7.

TABLE 7

| Ingredients | Amount % | g |
|---|---|---|
| SE | 87.5 | 33.0 |
| Unreacted fatty acid methyl ester | 3.7 | 1.4 |
| Soap | 5.3 | 2.0 |
| Fatty acid | 3.5 | 1.3 |
| Dimethylsulfoxide | — | 0.0 |
| Sucrose | — | 0.0 |
| Others | — | 0.0 |
| Total | 100.0 | 37.7 |

The filtrate contained a little amount of SE which had a monoester content of 86% and a higher ester content of 14%.

The slurry (weight: 150.8 g, solid content: 25%) was fed into a spray drying tower with keeping the temperature at 50° C. The conditions of spray drying were as follows:
Diameter of spray drying tower: 2.0 m
Length of true cylindrical portion: 1.5 m
Fed air: 360 N m³/hour
Diameter of rotary disk: 10 cm
Number of rotations of the disk: 24,000 r.p.m.
Temperature of air at inlet: 60° C.
Absolute humidity of air at inlet: 0.023 kg water/kg dry air Feeding velocity of slurry: 1.0 kg/hour The powdery SE obtained from the lower part of the spray drying tower had a water content of 1.81%, a bulk specific gravity of 0.41, no coloration due to heating and a good flowability.

The drying was continued stably, and there was no trouble such as sticking to the inner surface of the wall of the drying tower. The monoester content of the obtained SE was 68%, thus there was no change compared with that of SE before drying, and also there was no change in acid value.

EXAMPLE 6

The slurry (solid content: 25%) obtained in Example 5 was spray-dried in the same manner as in Example 5 except that the temperature of air at inlet was 40° C. and the feeding velocity of slurry was 0.5 kg/hour.

The obtained powdery SE had a water content of 1.92%, a bulk specific gravity of 0.42, a good flowability and no coloration due to heating. Also, the monoester content of the obtained SE was 68%, thus there was no change compared with that of SE before drying, and as to the acid value of the obtained SE, there was no change compared with that of SE before drying.

Further, there was no trouble such as sticking to the inner surface of the wall of the drying tower.

EXAMPLE 7

A reaction solvent was distilled away from the reaction mixture and neutralized with lactic acid in the same manner as in Example 1 to give the residue having the composition shown in Table 2.

Then, the residue was dried, and 100 kg of the thus dried matter was dissolved in 1000 kg water, salted-out, filtered and dried in the same manner as in Example 1 except that the amounts were 1000 times (kg), to give a cake having the composition shown in Table 3.

The filtrate (1180 kg) obtained in the above procedure was analyzed by GPC and found that SE was not contained therein and 75% of the reaction solvent was removed into the filtrate.

In 400 kg of an aqueous solution of acetic acid (pH 3.5) having room temperature was dispersed 80 kg of the thus obtained cake of which composition is described in Table 3. The dispersion was stirred in a homomixer for 10 minutes to uniformly break the precipitate into small particles, and was then filtered. This washing operation was repeated four times in total to give a purified precipitate having a water content of 41.2%.

The purified precipitate was adjusted to pH 7.4 with sodium hydroxide, and then water was added thereto to give a slurry having a solid content of 35%. To the same spray drying tower as used in Example 5 was fed 91.7 kg of the slurry and the dry-spraying was conducted under the same conditions as in Example 5 except that the temperature of air at inlet was 48° C., the absolute humidity of air at inlet was 0.015 kg water/kg dry air and the feeding velocity of slurry was 0.91 kg/hour.

The powdery SE obtained from the lower part of the spray drying tower was a white flowable powder and had a water content of 1.74%, a bulk specific gravity of 0.44 and no coloration due to heating. The drying was continued stably.

The composition of the obtained powdery SE is shown in Table 8.

TABLE 8

| Ingredients | Amount (%) |
| --- | --- |
| SE* | 86.7 |
| Unreacted fatty acid methyl ester | 4.1 |
| Soap | 5.7 |
| Fatty acid | 3.5 |
| Dimethylsulfoxide | (9.4 ppm) |
| Sucrose | 0.0 |
| Total | 100.0 |

(Note) *The stearate had a monoester content of 67.2% and a di- or higher-ester content of 32.8%

Then, water was added to 1,180 kg of the filtrate (the aqueous solution containing sucrose, the salts and the volatile materials, obtained after removing SE precipitate by the above-mentioned salting-out) to give an aqueous solution having the composition shown in Table 9.

TABLE 9

| Ingredients | Amount % | kg |
| --- | --- | --- |
| SE | 0.01 | 0.2 |
| Sucrose | 5.83 | 97.5 |
| Potassium lactate | 2.96 | 49.5 |
| Dimethylsulfoxide | 1.20 | 20.1 |
| Subtotal | 10.00 | 167.3 |
| Water | 90.00 | 1505.7 |
| Total | 100.00 | 1673.0 |

The aqueous solution was heated at 50° to 52.5° C., and was fed to a reverse osmosis membrane "SU-200" (Toray's trade mark) having a diameter of 4 inches, a length of 1 m and a filtrating area of 8 m² at a pump pressure of 58.2 kg/cm²G under the following operation conditions.
Discharge velocity of the aqueous solution passed through the reverse osmosis membrane:
  3.9 to 2.2 l/minute
Circulation velocity inside the membrane: 19.2 to 20.9 l/minute
Feeding time: about 550 minutes The concentrate which was not passed through the membrane contained sucrose, the salt derived from the catalyst and the volatile material in amounts of almost all, 46.0% and 52.0% of those included in the original reaction mixture, respectively. The composition of the concentrate is shown in Table 10.

On the other hand, the aqueous solution (i.e. filtrate) containing the salt derived from the catalyst and the volatile material, which was passed through the membrane had the composition shown in Table 10. As shown in Table 10, the filtrate scarcely contained sucrose, and contained the salt derived from the catalyst and the neutral salt and the volatile material in amounts of 54.0% and 48.0% of those included in the original reaction mixture, respectively.

TABLE 10

| Ingredients | Filtrate kg | % | Concentrate kg | % |
|---|---|---|---|---|
| SE | 0.0 | 0.0 | 0.2 | 0.2 |
| Unreacted sucrose | 0.0 | 0.0 | 97.5 | 74.4 |
| Potassium lactate*[1] | 26.7 | 73.5 | 22.8 | 17.4 |
| DMSO*[2] | 9.6 | 26.5 | 10.5 | 8.0 |
| Subtotal | 36.3 | 100.0 | 131.0 | 100.0 |
| Water | 588.7 | | 917.0 | |
| Total | 625.0 | | 1048.0 | |

(Note)
*[1]The salt derived from the catalyst
*[2]Dimethylsulfoxide (reaction solvent)

EXAMPLE 8

To 1,048 kg of the concentrate (solute concentration: 12.5%) having the composition shown in Table 10, obtained in Example 7 was added 1,900 kg of water and the thus obtained aqueous solution was fed into the same reverse osmosis membrance as used in Example 7 under the same conditions as in Example 7 to isolate sucrose.

The results are shown in Table 11.

TABLE 11

| Ingredients | Filtrate kg | % | Concentrate kg | % |
|---|---|---|---|---|
| SE | 0.0 | 0.0 | 0.2 | 0.02 |
| Unreacted sucrose | 0.0 | 0.0 | 97.5 | 96.13 |
| Potassium lactate*[1] | 15.7 | 68.2 | 7.1 | 0.70 |
| DMSO*[2] | 7.3 | 31.8 | 3.2 | 3.15 |
| Subtotal | 23.0 | 100.0 | 108.0 | 100.00 |
| Water | 1909.8 | | 907.2 | |
| Total | 1932.8 | | 1015.2 | |

(Notes)
*[1]The salt derived from the catalyst
*[2]Dimethylsulfoxide (reaction solvent)

EXAMPLE 9

To 1,015.2 kg of the concentrate (solute concentrate: 10.6%) shown in Table 11, obtained in Example 8 was added 2,200 kg of water and the thus obtained aqueous solution was fed into the same reverse osmosis membrane as used in Example 7 under the same conditions as in Example 7 to isolate sucrose. The results are shown in Table 12.

TABLE 12

| Ingredients | Filtrate kg | % | Concentrate kg | % |
|---|---|---|---|---|
| SE | 0.0 | 0.0 | 0.1 | 0.1 |
| Unreacted sucrose | 0.0 | 0.0 | 97.4 | 97.0 |
| Potassium lactate *[1] | 5.3 | 71.6 | 1.8 | 1.8 |
| DMSO*[2] | 2.1 | 28.4 | 1.1 | 1.1 |
| Subtotal | 7.4 | 100.0 | 100.4 | 100.0 |
| Water | 2197.4 | | 910.0 | |
| Total | 2204.8 | | 1010.4 | |

(Notes)
*[1]The salt derived from the catalyst
*[2]Dimethylsulfoxide (reaction solvent)

In addition to the ingredients used in the Examples, other ingredients can be used in the Examples as set forth in the specification to obtain substantially the same results.

What we claim is:

1. A process for removing a volatile material from a reaction mixture in synthesis of a sucrose fatty acid ester by a reaction of sucrose and a fatty acid alkyl ester in an organic solvent, said reaction mixture containing sucrose fatty acid ester, unreacted sucrose, unreacted fatty acid alkyl ester, a catalyst, a soap, a fatty acid and the organic solvent as a volatile material, which comprises adjusting the reaction mixture to a neutral pH region, adding water, a neutral salt and sucrose to the reaction mixture to transfer the volatile material into the aqueous phase with precipitation of the sucrose fatty acid ester, unreacted fatty acid alkyl ester, soap and fatty acid, and separating the resulting precipitate.

2. The process of claim 1, wherein said neutral region is from pH 6.2 to pH 8.2.

3. The process of claim 1, wherein after the addition of water, neutral salt and sucrose, the reaction mixture is heated to a temperature of 50° to 80° C.

4. The process of claim 1, wherein said water is added to the reaction mixture in a water/reaction mixture ratio of 5:1 to 40:1 by weight.

5. The process of claim 1, wherein the step of adding water, said neutral salt and sucrose further comprises adding the water, neutral salt and sucrose to the reaction mixture in amounts satisfying the following equations:

$$\frac{x}{y + x + z} = 0.015 \text{ to } 0.12$$

$$\frac{z}{y + x + z} = 0.025 \text{ to } 0.20$$

$$\frac{x}{z} = 0.4 \text{ to } 0.6$$

wherein x is the sum of the neutral salt to be added and a salt formed by neutralization of catalyst used in the synthesis of sucrose fatty acid ester, y is the total amount of water, and z is the sum of sucrose to be added and the unreacted sucrose present from the beginning.

6. The process of claim 1, wherein the pH adjustment of the reaction mixture is made with an acid selected from the group consisting of lactic acid, acetic acid, hydrochloric acid and sulfuric acid.

7. The process of claim 1, wherein said reaction mixture to be treated consists essentially of 15.0 to 92.0% by weight of a sucrose fatty acid ester, 1.0 to 80.0% by weight of unreacted sucrose, 0.5 to 10.0% by weight of unreacted fatty acid methyl ester, 0.05 to 7.0% by weight of a catalyst, 1.0 to 10.0% by weight of a soap, 0.5 to 10.0% by weight of a fatty acid and 5.0 to 30.0% by weight of a remaining reaction solvent.

8. The process of claim 1, wherein the fatty acid radical included in each of the fatty acid alkyl ester, soap and fatty acid is a saturated fatty acid radical having 16 to 22 carbon atoms.

9. The process of claim 1, wherein said volatile material is dimethylsulfoxide or dimethylformamide.

10. The process of claim 1, wherein said neutral salt to be added to the reaction mixture is a salt selected from the group consisting of sodium chloride, Glauber's salt, potassium lactate and potassium acetate.

11. The process of claim 1, wherein said sucrose fatty acid ester is composed of 10 to 75% by weight of the monoester and 90 to 25% by weight of the di- and higher esters.

12. A process for purifying a sucrose fatty acid ester included in a reaction mixture formed by a reaction of sucrose and a fatty acid alkyl ester in an organic solvent, which comprises adjusting the reaction mixture to a neutral pH region, adding water, a neutral salt and sucrose to the reaction mixture to precipitate the sucrose fatty acid ester, separating the resulting precipitate from the liquid phase, and washing the precipitate with an acidic water.

13. The process of claim 12, wherein said neutral pH region is from pH 6.2 to pH 8.2.

14. The process of claim 12, wherein after the addition of water, neutral salt and sucrose, the reaction mixture is heated to a temperature of 50° to 80° C.

15. The process of claim 12, wherein said water is added to the reaction mixture in a water/reaction mixture ratio of 5:1 to 40:1 by weight.

16. The process of claim 12, wherein the step of adding water, said neutral salt and sucrose further comprises adding the water, neutral salt and sucrose to the reaction mixture in amounts satisfying the following equations:

$$\frac{x}{y + x + z} = 0.015 \text{ to } 0.12$$

$$\frac{z}{y + x + z} = 0.025 \text{ to } 0.20$$

$$\frac{x}{z} = 0.4 \text{ to } 0.6$$

wherein x is the sum of the neutral salt to be added and a salt formed by neutralization of catalyst used in the synthesis of sucrose fatty acid ester, y is the total amount of water, and z is the sum of sucrose to be added and the unreacted sucrose present from the beginning.

17. The process of claim 12, wherein said acidic water has a pH of 3.0 to 5.5.

18. The process of claim 12, wherein said acidic water is maintained at a temperature of 10° to 40° C.

19. The process of claim 12, wherein said precipitate washed with the acidic water is neutralized and spray-dried in the form of an aqueous slurry.

20. The process of claim 19, wherein said slurry has a solid content of 4 to 40% by weight and a water content of 96 to 60% by weight.

21. The process of claim 19, wherein said spray-drying is conducted in an air stream having an absolute humidity of 0.008 to 0.05 kg water/kg dry air and a temperature of 10° to 100° C.

22. The process of claim 12, wherein said liquid phase is brought into contact with a reverse osmosis membrane to recover sucrose.

23. The process of claim 22, wherein said reverse osmosis membrane has a fractionation molecular weight of 150 to 200.

24. The process of claim 22, wherein said liquid to be contacted with the membrane is maintained at a temperature of 40° to 60° C.

25. The process of claim 22, wherein said liquid to be contacted with the membrane is maintained at a pH of 6.2 to 8.2.

* * * * *